United States Patent
Suzuki et al.

(10) Patent No.: US 6,313,074 B1
(45) Date of Patent: Nov. 6, 2001

(54) EFFECT ENHANCER FOR AGRICULTURAL CHEMICAL

(75) Inventors: Tadayuki Suzuki; Masaharu Hayashi; Kazuhiko Kurita; Yuichi Hioki, all of Wakayama (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 09/462,269

(22) PCT Filed: Jul. 10, 1998

(86) PCT No.: PCT/JP98/03111

§ 371 Date: Apr. 3, 2000

§ 102(e) Date: Apr. 3, 2000

(87) PCT Pub. No.: WO99/03345

PCT Pub. Date: Jan. 28, 1999

(30) Foreign Application Priority Data

Jul. 15, 1997 (JP) .................................................. 9-189810

(51) Int. Cl.⁷ .................................................... A01N 25/30
(52) U.S. Cl. ........................... 504/362; 514/772; 514/975
(58) Field of Search ............................ 504/362; 514/772, 514/975

(56) References Cited

U.S. PATENT DOCUMENTS 4,313,847 * 2/1982 Chasin et al. ....................... 252/356

FOREIGN PATENT DOCUMENTS

| A20355759 | 2/1990 | (EP) . |
|---|---|---|
| 0681865A2 | 11/1995 | (EP) . |
| 2111966 | 6/1972 | (FR) . |
| 1371770 | 10/1974 | (GB) . |
| 1601652 | 11/1981 | (GB) . |
| A2-174707 | 7/1990 | (JP) . |
| A7-308561 | 11/1995 | (JP) . |

* cited by examiner

*Primary Examiner*—S. Mark Clardy
(74) *Attorney, Agent, or Firm*—Birch, Stewart, Kolasch & Birch, LLP

(57) ABSTRACT

There are provided an effect enhancer for an agricultural chemical and an a chemical formulation which is not pharmaceutically harmful to various crops and can be safely used and which has an excellent effect enhancing function to various agricultural chemicals. The effect enhancer for the agricultural chemical comprises, as an effective component, a compound represented by the following formula (I): $R—O[(EO)_x(PO)_y](EO)_z—H$, wherein EO is an oxyethylene group; PO is an oxypropylene group; R is a straight-chin or branched alkyl group or alkenyl group having 6 to 30 carbon atoms; x is a value of 1 to 30 on the average; y is a value of 1 to 30 on the average, and z is a value of 1 to 30 on the average. The agricultural chemical formulation composes the above-mentioned surfactant and a technical grade of active ingredient or an active compound for an agricultural chemical.

12 Claims, No Drawings

EFFECT ENHANCER FOR AGRICULTURAL CHEMICAL

This application is the national phase under 35 U.S.C. §371 of PCT International Application No. PCT/JP98/03111 which has an International filing date of Jul. 10, 1998, which designated the United States of America.

TECHNICAL FIELD

The present invention relates to a novel effect enhancer for an agricultural chemical, an agricultural chemical formulation, an agricultural chemical composition, and a method for enhancing the effect of the agricultural chemical.

BACKGROUND ART

Agricultural chemicals such as insecticides, bactericides, herbicides, acaricides and plant growth moderators have been used in the forms of emulsions, hydrates, particles, powders and flowables. In this case, in order to sufficiently obtain the effects of a technical grade of active ingredient or an active compound for an agricultural chemical, various contrivances regarding the formulation and physical properties of the agricultural chemicals have been made, but it is now difficult to further enhance the effects of the agricultural chemicals by the contrivances of their formulation.

Furthermore, since the development of a novel agricultural chemical is more difficult, it is industrially meaningful to further enhance the activity of the already existing agricultural chemicals.

DISCLOSURE OF THE INVENTION

The present inventors have intensively investigated with the intention of developing an effect enhancer for an agricultural chemical by which the effect of the agricultural chemical can be enhanced by combining it with a technical grade of active ingredient or an active compound for an agricultural chemical, and a method for enhancing the effect of the agricultural chemical. As a result, it has been found that a specific polyoxyalkylene-having surfactant has an effect enhancement function particularly to various agricultural chemicals, and the present invention has been completed.

That is to say, the present invention provides an effect enhancer for an agricultural chemical containing a compound represented by the formula (I) as an effective component. Further, the present invention provides a method for enhancing the effect of the agricultural chemical by feeding the above-mentioned effect enhancer for the agricultural chemical and the agricultural chemical to a site where the effect of the agricultural chemical is necessary;

$$R\text{—}O[(EO)_x(PO)_y](EO)_z\text{—}H \quad (I)$$

wherein EO is an oxyethylene group; PO is an oxypropylene group; R is a straight-chain or branched alkyl group or alkenyl group having 6 to 30 carbon atoms; x is a value of 1 to 30 on the average; y is a value of 1 to 30 on the average; and z is a value of 1 to 30 on the average.

Furthermore, the present invention provides a composition containing a compound represented by the formula (I) and a technical grade of active ingredient or an active compound for an agricultural chemical, i.e., an agricultural chemical formulation and an agricultural chemical composition.

Besides, the present invention provides use of the compound represented by the formula (I) as the effect enhancer for an agricultural chemical.

Here, a copolymer represented by the formula $[(EO)_x(PO)_y]$ may be a random copolymer or a block copolymer of ethylene oxide and propylene oxide. The compound represented by the formula (I) can be manufactured by adding ethylene oxide and propylene oxide to an alcohol R—OH. In short, in a typical case, x mol of ethylene oxide may be added to 1 mol of the alcohol R—OH, and y mol of propylene oxide may be then added thereto, and z mol of ethylene oxide may be lastly added thereto. Alternatively, x mol of ethylene oxide and y mol of propylene oxide may be mixed with each other, and the resultant mixture may be then reacted with the alcohol R—OH.

As the compound represented by the formula (I) which is contained as an effective component in the effect enhancer of the present invention, a compound in which R is a straight-chain or branched alkyl group or alkenyl group having 8 to 20 carbon atoms is preferable. Furthermore, it is preferable that x and z in the formula (I) are each a value of 1 to 10 on the average.

Mechanisms, in which the effect enhancer for the agricultural chemical of the present invention assumes a remarkable effect enhancement function irrespective of the kind of structure of the agricultural chemical, have not been definitely clarified, but one of the mechanisms can be presumed to be that since the dissolving power of the effect enhancer of the present invention is very high, the agricultural chemical can be ground into fine particles to accelerate its impregnation into plants, insects or bacteria. The form of the effect enhancer for the agricultural chemical of the present invention may be any of a liquid, a powder and particles, and the form of the effect enhancer is not restrictive.

A method of using the effect enhancer for the agricultural chemical regarding the present invention and a method for enhancing the effect of the agricultural chemical include a method of using a composition containing the effect enhancer for the agricultural chemical, i.e., an agricultural chemical formulation and an agricultural chemical composition, and a method of using the effect enhancer for the agricultural chemical at the time of the dilution of an agricultural chemical (not containing the effect enhancer of the present invention), but by the use of either of these methods, an effect enhancement function which is intended by the present invention can be obtained. Furthermore, the effect enhancer for the agricultural chemical regarding the present invention is not pharmaceutically harmful to various crops, and so it can be safely used.

When the effect enhancer for the agricultural chemical of the present invention is blended with a prevalent agricultural chemical for a plant or an animal and then used as the agricultural chemical formulation and the agricultural chemical composition, or when the effect enhancer for the agricultural chemical is used together with the above-mentioned agricultural chemical, its extermination effect can be improved remarkably. In addition, the effect enhancer for the agricultural chemical of the present invention also has a high safety. Hence, since the activity of the already existing agricultural chemical can be improved by the use of the effect enhancer for the agricultural chemical of the present invention, the choices of the agricultural chemicals to be used by a producer can be increased. Therefore, various advantages can be expected by using an agricultural chemical which is poor in the effect but which is inexpensive or highly safe.

The present invention provides a composition containing at least one of compounds represented by the formula (I) and another surfactant. Moreover, the present invention provides a method for feeding the compound represented by the formula (I) and the above-mentioned surfactant to a site where the effect of the agricultural chemical is required. According to this method, the use amount of the compound represented by the formula (I) can be reduced, while the effect enhancement of the agricultural chemical is maintained. As the surfactant, a nonionic surfactant, an anionic surfactant, a cationic surfactant, an amphoteric surfactant or a mixture thereof can be used.

Examples of the nonionic surfactant include polyoxyethylene alkyl ethers, polyoxyethylene alkylaryl ethers, polyoxyethylene alkylaryl ether formaldehyde condensates, polyoxyalkylene aryl ethers, polyoxyalkylene alkyl esters, polyoxyalkylene alkylsorbitol esters, polyoxyalkylene sorbitan esters, polyoxyalkylene alkylglycerol esters, polyoxyalkylene block copolymers, polyoxyalkylene block copolymer alkyl glycerol esters, polyoxyalkylene alkylsulfonamides, polyoxyalkylene rosin esters, polyoxypropylene block copolymers, polyoxyethylene oleyl ethers, polyoxyalkylene alkylphenols, alkyl glycosides, alkyl polyglycosides and polyoxyalkylene alkylpolyglycosides. These surfactants may be used singly or in a mixture of two or more thereof.

Examples of the cationic surfactant include polyoxyethylene alkylamine, polyoxypropylene alkylamine, for example, polyoxyethylene tallow amine, polyoxyethylene oleylamine, polyoxyethylene soy amine, polyoxyethylene cocoamine, synthetic polyoxyethylene alylamine, polyoxyethylene octylamine, alkanolamine alkyl ester compounds mentioned in WO 95/33379, polyoxyalkylene thereof, quaternary ammonium compounds derived from these compounds, and mixtures thereof.

Typical products of the anionic surfactants are available in the states of aqueous solutions and powders, and their examples include sodium mono- or di-alkylnaphthalenesulfonates, sodium α-olefinsulfonates, sodium alkanesulfonates, alkylsulfosuccinates, alkylsulfates, polyoxyalkylene alkyl ether sulfates, polyoxyalkylene alkylaryl ether sulfates, polyoxyalkylene styrylphenyl ether sulfates, mono- or di-alkylbenzene sulfonates, alkylnaphthalene sulfonates, sodium naphthalene sulfonate formaldehyde condensate, alkyldiphenyl ether sulfonates, olefinic sulfonates, mono- or di-alkylphosphates, polyoxyalkylene mono- or di-alkylphophates, polyoxyalkylene mono- or di-phenyl ether phosphates, polyoxyalkylene mono- or di-alkylphenyl ether phosphates, polycarbonates, salts of fatty acids, straight-chain or branched alkylpolyoxyalkylene ether acetic acids and their salts, alkenylpolyoxyalkylene ether acetic acids and their salts, stearic acid and its salts, oleic acid and its salts, N-methylfatty acid taurides, and mixtures of two or more thereof (including sodium, potassium, ammonium and amine salts).

In addition, examples of the amphoteric surfactant include lauryldimethylamine oxide, Armox C/12, amine oxides, Monaterics, Miranols, betaine, Lonzaines, other amine oxides and mixtures thereof.

Among these surfactants, the nonionic surfactants and the anionic surfactants are particularly preferable.

In the effect enhancer for the agricultural chemical containing the compound represented by the above-mentioned formula (I) and the other surfactant as effective components, a ratio of the total weight of the compound represented by the formula (I) to the surfactant is preferably [the total weight of the compound represented by the formula (I)]/[the surfactant other than this compound]=1/10 to 50/1 (weight ratio), more preferably 1/1 to 10/1.

The present invention provides a composition obtained by containing at least one of compounds represented by the formula (I) with a chelating agent. Examples of this chelating agent include aminopolycarboxylic acid chelating agents, aromatic and aliphatic carboxylic acid chelating agents, amino acid chelating agents, ether polycarboxylic acid chelating agents, phosphonic acid chelating agents [e.g., iminodimethylphosphonic acid (IDP) and alkyldiphosphonic acid (ADPA)], and dimethylglyoxime (DG), and they may be used in the state of these existing acids and in the form of salts of sodium, potassium and ammonium. In the present invention, the amount of the chelating agent is in the range of 0.01 to 30 mols, preferably 0.05 to 20 mols, more preferably 0.1 to 15 mols per mol of the compound presented by the formula (I).

As the aminopolycarboxylic acid chelating agents, there can be used all of (a) $RNX_2$ type compounds, (b) $NX_3$ type compounds, (c) $R-NX-CH_2CH_2-NX-R$ type compounds, (d) $R-NX-CH_2CH_2-NX_2$ type compounds, and (e) $X_2N-R'-NX_2$ type and compounds of this type containing 4 or more Xs.

In the above-mentioned formulae, X is $-CH_2COOH$ or $-CH_2CH_2COOH$, R is a hydrogen atom, an alkyl group, a hydroxyl group, a hydroxyalkyl group or a substituent representing this kind of known chelating compound, R' is an alkylene group, a cycloalkylene group or a substituent representing this kind of known chelating compound. Typical examples of these compounds include ethylenediaminetetraacetic acid (EDTA), cyclohexanediaminetetraacetic acid (CDTA), nitrilotriacetic acid (NTA), iminodiacetic acid (IDA), N-(2-hydroxyethyl)iminodiacetic acid (HIMDA), diethylenetriaminepentaacetic acid (DTPA), N-(2-hydroxyethyl)ethylenediaminetetraacetic acid (EDTA—OH), glycol ether diaminetetraacetic acid (GEDTA) and salts thereof.

Examples of the aromatic and aliphatic carboxylic acid chelating agents include citric acid, oxalic acid, glycolic acid, pyruvic acid, anthranilic acid and salts thereof.

Examples of the amino acid chelating agents include glycine, serine, alanine, lysine, cystine, cysteine, ethionine, tyrosine, methionine, and salts and derivatives thereof. In addition, examples of the ether polycarboxylic acid chelating agents which can be used in the present invention include compounds represented by the following formula, similar compounds and salts thereof (particularly Na salts).

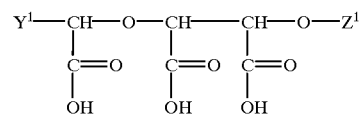

[wherein Y and Z mean as follows:
$Y^1 = -H, -CH_2COOH$ or $-COOH$
$Z^1 = -H, -CH_2COOH$ or $-CHCOOH$
                                  $|$
                                  $CH_2COOH$]

The agricultural chemical formulation of the present invention comprises the compound represented by the formula (I) and the technical grade of active ingredient or the active compound for an agricultural chemical. Here, the technical grade of active ingredient or the active compound for an agricultural chemical means an effective component of the agricultural chemical. In the formulation of the present invention, it is necessary that a weight ratio of the compound represented by the formula (I) to the technical grade of active ingredient or the active compound for an agricultural chemical should be [the compound represented by the formula (I)]/[the technical grade of active ingredient or the active compound for an agricultural chemical]=0.03 to 50, preferably 0.04 to 20, more preferably 0.1 to 10. If this ratio is less than 0.03, the effect enhancement function of the agricultural chemical cannot sufficiently be attained. On the other hand, even if it is more than 50, a further effect cannot be expected.

Furthermore, the form of the agricultural chemical formulation of the present invention is not restrictive, and they can take any of an emulsion, a hydrate, particles, a powder and a flowable. Therefore, the agricultural chemical formulation may contain other additives such as an emulsifier, a dispersant and a carrier in compliance with the selected form.

To the agricultural chemical formulation of the present invention, a chelating agent, a pH adjustor, an inorganic salt and a thickener may be added, if necessary.

As examples of the chelating agent, the same compounds as used in the effect enhancer for the agricultural chemical can be used.

Examples of the pH adjustor which can be used in the present invention include citric acid, phosphoric acid (pyrophosphoric acid), gluconic acid and salts thereof.

Examples of the inorganic salt which can be used in the present invention include inorganic mineral salts such as inorganic salt clays, talcs, bentonites, zeolites, calcium carbonate, diatomaceous earth and white carbon, and inorganic ammonium salts such as an ammonium sulfate, an ammonium nitrate, an ammonium phosphate, an ammonium thiocyanate, an ammonium chloride and an ammonium sulfamate.

As the thickener which can be used in the present invention, all of natural, semisynthetic and synthetic water-soluble thickeners can be used. Examples of the thickener include natural thickeners such as xanthan gum derived from microorganisms, pectin, arabic gum and cyamoposis gum derived from plants, semisynthetic thickeners such as methylated compounds of cellulose and starch derivatives, calboxyalkylated compounds, hydroxyalkylated compounds (including methyl cellulose, carboxymethyl cellulose, hydroxymethyl cellulose and the like) and sorbitols, and synthetic thickeners such as polyacrylates, polymaleates, polyvinylpyrrolidones and pentaerythritol ethylene oxide adducts.

Next, examples of the technical grade of active ingredient or the active compound for an agricultural chemical which can be used in the agricultural chemical formulation of the present invention will be mentioned, but the scope of the present invention should not be limited to these examples.

Examples of the bactericides include Dithane (zinc ethylene bisdithiocarbamate), maneb (manganese ethylene bisdithiocarbamate), thiram (bis(dimethylthiocarbamoyl) disulfide), mancozeb (zinc ion-coordinated manganese ethylenebisdithiocarbamate), Bis-Dithane (bisdimethyldithiocarbamoylzinc ethylenebisdithiocarbamate), propineb (zinc propylenebisdithiocarbamate), benzimidazole-based bactericides such as benomyl (methyl-1-(butylcarbamoyl)-2-benzimidazole carbamate) and thiophanate-methyl (1,2-bis (3-methoxycarbonyl-2-thioureido)benzene, vinclozolin (3-(3,5-dichlorophenyl)-5-methyl-5-vinyl-1,3-oxazolidine-2,4-dione), iprodione (3-(3,5-dichlorophenyl)-N-isopropyl-2,4-dioxoimidazolidine-1-carboxamide), procymidone (N-(3,5-dichlorophenyl)-1,2-dimethylcyclopropane-1,2-dicarboxyimide), Triasyn (2,4-dichloro-6-(2-chloroanilino)-1,3,5-triazin), triflumizole ((E)-4-chloro-α,α,α-trifluoro-N-(1-imidazol-1-yl-2-propoxyethylidene)-o-toluidine), metalaxyl (methyl-N-(2-methoxyacetyl)-N-(2,6-xylyl)-D,L-alaninate), bitertanol (all-rac-1-(biphenyl-4-yloxy)-3,3-dimethyl-1-(1H-1,2,4-triazol-1-yl)-2-butan-2-ol), pyrifenox (2,4-dichloro-2-(3-pyridyl)acetophenone-(EZ)-O-methyloxime), fenarimol (2,4-dichloro-α-(pyrimidin-5-yl) benzhydryl=alcohol), triforine (1,4-bis-(2,2,2-trichloro-1-formamidoethyl)piperazine), guazatine iminoctadine (1,1-iminiodi(octamethylene)diguanidinium triacetate), organocopper compound (Oxine-copper), antibiotic bactericides (streptomycins, tetracyclines, polyoxy series, blasticidin S, kasugamycins and validamycins), triadimefon (1-(4-chlorophenoxy)-3,3-dimethyl-1-(1,2,4-triazol-1-yl)-2-butanone), isoprothiolane (diisopropyl-1,3-dithiolane-2-ylidene malonate), Daconil (tetrachloroisophthalonitrile), Pansoil (5-ethoxy-3-trichloromethyl-1,2,4-thiadiazole), fthalide (4,5,6,7-tetrachlorophthalide), Kitazin P (O,O-diisopropyl-S-benzyl thiophosphate), Hinosan (O-ethyl-S,S-diphenyl dithiophosphate), probenazole (3-allyloxy-1,2-benzisothiazole-1,1-dioxide), captan (N-trichloromethylthio-tetrahydrophthalimide) and fosetyl (aluminum=tris(ethyl=phosphonate)).

Examples of the insecticides include pyrethroid-containing insecticides such as fenvalerate (α-cyano-3-phenoxybenzyl-2-(4-chlorophenyl)-3-methylbutanoate) and Baythroid (cyano(4-fluoro-3-phenoxyphenylmethyl-3-(2,2-dichloroethenyl)-2,2-dimethylcyclopropane carboxylate), organic phosphorus-containing insecticides such as DDVP (dimethyl-2,2-dichlorovinyl phosphate), Sumithion (MEP) (O,O-dimethyl-O-(3-methyl-4-nitrophenyl) thiophosphate), Malathon (S-[1,2-bis(ethoxycarbonyl)ethyl] dimethylphosphorothiol thionate), dimethoate (dimethyl-S-(N-methylcarbamoylmethyl) dithiophosphate), Elsan (S-[α-(ethoxycarbonyl)benzyl]dimethylphosphorothiol thionate) and Baycid (O,O-dimethyl-O-(3-methyl-4-methylthiophenyl) thiophosphate)), carbamate-containing insecticides such as Bassa (O-sec-butylphenylmethyl carbamate), MTMC (m-trimethyl carbamate), Meobar (3,4-dimethylphenyl-N-methyl carbamate) and NAC (1-naphthyl-N-methyl carbamate), methomyl (S-methyl-N [(methyl carbamoyl)oxy]thioacetimide) and cartap (1,3-bis (carbamoylthio)-2-(N,N-dimethylamino)propane hydrochloride).

In addition, examples of the natural insecticides include pyrethrins derived from insect flowers, piperonyl butoxide, rotenones derived from derris; shrubs of Fabaceae and nicotines (3-(1-methyl-2-pyrrolidinyl)pyridine sulfate). Examples of the insect grown regulators (IGR agents) include diflubezuron (1-(4-chlorophenyl)-3-(2,6-difluorobenzoyl)urea), teflubenzuron (1-(3,5-dichloro-2,4-difluorophenyl)-3-(2,6-difluorobenzoyl)urea), chlorfluazuron (1-[3,5-dichloro-4-(3-chloro-5-trifluoromethyl-2-pyridyloxy)phenyl]-3-(2,6-difluorobenzoyl)urea, buprofezin (2-tertiary-butylimino-3-isopropyl-5-phenyl-3,4,5,6-tetrahydro-2H-1,3,5-thiadiazin-4-one) and fenoxycarb (ethyl-2-(4-phenoxyphenoxy)ethyl carbamate). The IGR agents are particularly preferable.

Furthermore, examples of the acaricides include pyridaben (2-tert-butyl-5-(4-tert-butylbenzylthio)-4-chloropyridazine-3(2H)-one), Acricid (2,4-dinitro-6-secondary-butylphenyldimethyl acrylate), Chloromite (isopropyl-4,4-dichlorobenzilate), Akar (ethyl-4,4-dichlorobenzilate), Kelthane (1,1 -bis(p-chlorophenyl)-2,2,2-trichloroethanol), Citrazon (ethyl-O-benzoyl-3-chloro-2,6-dimethoxybenzohydroxymate), Omite (2-(p-tert-butylphenoxy)-cyclohexyl-2-propynyl sulfite), Osadan (hexakis(β,β-dimethylphenylethyl)distannoxane), hexythiazox (trans-5-(4-chlorophenyl)-N-cyclohexyl-4-methyl-2-oxothiazolidine-3-carboxamide), amitraz (3-methyl-1,5-bis(2,4-xylyl)-1,3,5-triazapenta-1,4-diene).

Examples of the herbicides include acid amide-containing herbicides such as Stam (3,4-dichloropropionanilide, DCPA) and alachlor (2-chloro-2',6'-diethyl-N-(methoxymethyl)acetanilide); urea-containing herbicides such as DCMU (3-(3,4-dichlorophenyl)-1,1-dimethylurea) and linuron (3-(3,4-dichlorophenyl)-1-methoxy-1-methylurea); dipyridyl-containing herbicides such as paraquat (1,1'-dimethyl-4,4'-bipyridium dichloride) and diguat (6,7-dihydrodipyrido[1,2-a:2',1'c] pyranzinediium dibromide); diazine-containing herbicides such as bromacil (5-bromo-3-sec-butyl-6-methyluracil); S-triazine-containing herbicides such as simazine (2-chloro-4,6-bis (ethylamino)-1,3,5-triazine and simetryn (2,4-bis (ethylamino)-6-methylthio-1,3,5-triazine; nitrile-containing herbicides such as DBN (2,6-dichlorobenzonitrile); dinitroaniline-containing herbicides such as trifluralin (α,α,α-trifluoro-2,6-dinitro-N,N-dipropyl-p-toluidine); carbamate-containing herbicides such as benthiocarb (Saturn) (S-p-chlorobenzyl-N,N-diethyl thiocarbamate and MCC (methyl-3,4-dichlorocarbonilate); diphenyl ether-containing herbicides such as NIP (2,4-dichlorophenyl-p-nitrophenyl ether); benzoic acid-containing herbicides such as MDBA (dimethylamine-3,6-dichloro-o-anisilate); phenoxy-containing herbicides such as 2,4-D sodium salt (sodium 2,4-dichlorophenoxy acetate), Mapica ([(4-chloro-o-tolyl)oxy]aceto-o-chloroanilide); organic phosphorus-containing herbicides such as glyphosate (N-phosphonomethyl)glycine or its salt), bialaphos (sodium salt of L-2-amino-4-[(hydroxy)(methyl)=phosphinoyl] butyryl-L-alanyl-L-alanine) and glufosinate (ammonium-DL-homoalanin-4-yl(methyl) phosphinate); aliphatic herbicides such as Na salt of TCA (sodium trichloroacetate); sulfonylurea-containing herbicides such as thifensulfuron-methyl [methyl-3-(4-methoxy-6-methyl-1,3,5-triazin-2-ylcarbamoylsulfamoyl)-2-thenoate] and flazasulfuron [1-(4,6-dimethoxypyrimidine-2-yl)-3-(3-trifluormethyl-2-pyridylsulfonyl)urea].

Among these herbicides, the acid amide-containing herbicides, the diazine-containing herbicides, the nitrile-containing herbicides, the dinitroaniline-containing herbicides, the benzoic acid-containing herbicides and the organic phosphorus-containing herbicides are preferable, and the organic phosphorus-containing herbicides are particularly preferable. Above all, bialaphos (sodium salt of L-2-amino-4-[(hydroxy)(methyl)=phosphinoyl]butyryl-L-alanyl-L-alanine), glufosinate (ammonium-DL-homoalanin-4-yl(methyl) phosphinate) and glyphosate (N-(phosphonomethyl)glycine or its salt) are preferable.

Moreover, examples of the plant growth moderators include MH (maleic hydrazide), Ethrel (2-chloroethylphosphonic acid), UASTA and bialaphos.

In addition, the agricultural chemical composition of the present invention can be mixed with one or more of a plant growth moderator other than mentioned above, a fertilizer, an antiseptic agent and the like, prior to its use.

In the present invention, for the purpose of a bacteria killing, an insect killing, an acarid killing, a weed killing or a plant growth moderation, the agricultural chemical formulation is used which contains the effect enhancer for the agricultural chemical regarding the present invention in an amount 0.03 to 50 times, preferably 0.04 to 20 times, more preferably 0.1 to 10 times as much as the technical grade of active ingredient or the active compound for an agricultural chemical.

Typical examples of the agricultural chemical formulations according to the present invention include (a) an agricultural chemical formulation comprising a separate package of one or more of the compounds represented by the above-mentioned formula (I), and a separate package of the technical grade of active ingredient or the active compound for an agricultural chemical, (b) an agricultural chemical formulation comprising a separate package of a mixture of one or more of the compounds represented by the above-mentioned formula (I) and one or more of surfactants other than these compounds, and a separate package of the technical grade of active ingredient or the active compound for an agricultural chemical, (c) an agricultural chemical formulation comprising a separate package of one or more of the compounds represented by the above-mentioned formula (I), a separate package of one or more of surfactants other than these compounds, and a separate package of the technical grade of active ingredient or the active compound for an agricultural chemical, (d) an agricultural chemical formulation comprising a separate package of a mixture of one or more of the compounds represented by the above-mentioned formula (I) and a chelating agent, and a separate package of the technical grade of active ingredient or the active compound for an agricultural chemical, (e) an agricultural chemical formulation comprising a separate package of a mixture of one or more of the compounds represented by the above-mentioned formula (I) and a chelating agent, a separate package of one or more of surfactants other than these compounds, and a separate package of the technical grade of active ingredient or the active compound for an agricultural chemical, and (f) an agricultural chemical formulation comprising a separate package of a mixture of one or more of the compounds represented by the above-mentioned formula (I), one or more of surfactants other than these compounds and a chelating agent, and a separate package of the technical grade of active ingredient or the active compound for an agricultural chemical. The form of the respective packages is not restricted, and they can be prepared in compliance with a use and a purpose.

In the present invention, an emulsifier for the agricultural chemical or a dispersant for the agricultural chemical containing the compound represented by the above-mentioned formula (I) as an effective component can be used. That is to say, the agricultural chemical formulation having excellent emulsifying properties and dispersing properties can be obtained by blending the water-insoluble technical grade of active ingredient or active compound for an agricultural chemical with the compound represented by the formula (I) and if necessary, a solvent acceptable in the preparation of the agricultural chemical formulation, a suitable anionic surfactant or nonionic surfactant.

In the water-insoluble technical grade of active ingredient or active compound for an agricultural chemical, examples of the insecticides include pyrethroid-containing insecticides such as fenvalerate [α-cyano-3-phenoxybenzyl-2-(4-chlorophenyl)-3-methylbutanoate] and Baythroid [cyano(4-fluoro-3-phenoxyphenylmethyl-3-(2,2 -dichloroethenyl)-2,2-dimethylcyclopropane carboxylate, organic phosphorus-containing insecticides such as DDVP (dimethyl-2,2- dichlorovinyl phosphate), Sumithion (MEP) (O,O-dimethyl-O-(3-methyl-4 -nitrophenyl) thiophosphate), Malathon [S-{1,2-bis(ethoxycarbonyl)ethyl}dimethylphosphorothiol thionate], dimethoate [dimethyl-S-(N-methylcarbamoylmethyl) dithiophosphate], Elsan [S-{α-(ethoxycarbonyl)benzyl}dimethylphosphorothiol thionate] and Baycid (O,O-dimethyl-O-(3-methyl-4-methylthiophenyl thiophosphate)], carbamate-containing insecticides such as Bassa (O-sec-butylphenylmethyl carbamate), MTMC (m-trimethyl carbamate), Meobar (3,4-dimethylphenyl-N-methyl carbamate) and cartap [1,3-bis(carbamoylthio)-2-(N,N-dimethylamino)propane hydrochloride]. Furthermore, examples of the acaricides include pyridaben [2-tert-butyl-5-(4-tert-butylbenzylthio)-4-chloropyridazine-3(2H)-one], Acricid (2,4-dinitro-6-sec-butylphenyldimethyl acrylate), Chloromite (isopropyl-4,4-dichlorobenzilate), Akar (ethyl-4,4-dichlorobenzilate), Kelthane [1,1-bis(p-chlorophenyl)-2,2,2-trichloroethanol], Citrazon (ethyl-O-benzoyl-3-chloro-2,6-dimethoxybenzohydroxymate), Omite [2-(p-tert-butylphenoxy)-cyclohexyl-2-propynyl sulfite], Osadan [hexakis(β,β-dimethylphenylethyl)distannoxane], hexythiazox [trans-5-(4-chlorophenyl)-N-cyclohexyl-4-methyl-2-oxothiazolidine-3-carboxamide], amitraz [3-methyl-1,5-bis (2,4-xylyl)-1,3,5-triazapenta-1,4-diene] and purified machine oils.

In the present invention, for the purpose of the stable emulsifying properties and dispersing properties of the water-insoluble technical grade of active ingredient or active compound for an agricultural chemical, the emulsifier agent for the agricultural chemical or the dispersant for the agricultural chemical is blended, and a blend ratio of the emulsifier for the agricultural chemical or the dispersant for the agricultural chemical to the water-insoluble technical grade of active ingredient or active compound for an agricultural chemical is preferably 0.002 to 1.0 weight time, particularly preferably 0.01 to 0.5 weight time as much as the water-insoluble technical grade of active ingredient or active compound for an agricultural chemical.

EXAMPLES

Next, the present invention will be described in accordance with examples, but the scope of the present invention is not limited to these examples.

Example 1

Various effect enhancers for agricultural chemicals shown in Table 2 were prepared by the use of compounds selected from Table 1 and if necessary, surfactants (B) and chelating agents (C) shown in Table 2. Furthermore, a chemical formula of the used chelating agents is shown in the following.

$R^1$—O[$(EO)_x(PO)_y(EO)_z$]—H

TABLE 1

| Compound No | $R^1$ | x | y | z |
|---|---|---|---|---|
| ① | tallow alkyl | 2.5 | 5 | 3 |
| ② | $C_{12}/C_{14}$* | 5 | 1.5 | 5 |
| ③ | coco alkyl | 7 | 1.5 | 7 |
| ④ | oleyl | 10 | 8 | 10 |

*$C_{12}/C_{14}$ = 70/30 (wt/wt)

TABLE 2

| Effective component No. | Compound No (A) | Surfactant (B) and/or a chelating agent (C) to be used together | (A)/(B)/(C) weight ratio |
|---|---|---|---|
| 1 | ① | — | 100/0/0 |
| 2 | ① | POE(20) sorbitan monooleate | 80/20/0 |
| 3 | ① | Decyl polyglycoside (polymerization degree: 1.3) | 80/20/0 |
| 4 | ① | EDTA | 90/10/0 |
| 5 | ① | POE(20) sorbitan monooleate EDTA | 80/10/10 |
| 6 | ② | — | 100/0/0 |
| 7 | ② | POE(10) rosin ester | 80/20/0 |
| 8 | ② | POE(11) oleic acid ester | 80/20/0 |
| 9 | ② | NTA | 80/20/0 |
| 10 | ② | POE(10) Sodium lauryl ether sulfate | 80/20/0 |
| 11 | ② | — | 100/0/0 |
| 12 | ③ | POE(9) sodium cocoalkylacetate | 80/20/0 |
| 13 | ③ | POE(4) oleyl ether | 80/20/0 |
| 14 | ③ | Naphthalene sulfonate formaldehyde condensate | 80/20/0 |
| 15 | ③ | POE(10) triethanolamine lauryl ether sulfate | 80/20/0 |
| 16 | ④ | — | 100/0/0 |
| 17 | ④ | POE(15) cocoalkyl monomethylammonium chloride | 80/20/0 |
| 18 | ④ | POE(15) cocoalkyl monomethylammonium chloride/EDTA | 80/10/10 |
| 19 | ④ | POE(20) sorbitan monooleate | 80/20/0 |
| 20 | ④ | Sorbitan monooleate | 70/30/0 |
| 21 | POE(10) nonylphenyl ether | | |
| 22 | POE(20) nonylphenyl ether | | |

(Note) POE is an abbreviation of polyoxyethylene, and a value in each parenthesis means an average additional mol number of ethylene oxide.

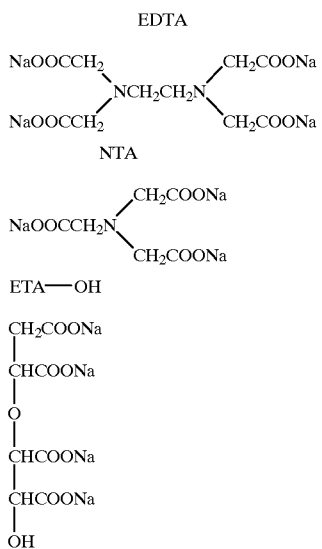

Each of the above-mentioned effect enhancers for agricultural chemicals was dissolved in ion-exchanged water so as to prepare a 0.2% by weight diluted solution. With the thus obtained 0.2% by weight diluted solution, each of a round-up solution (an effective content of a glyphosate isopropylamine salt=41% by weight), a Banvel D solution (an effective content of an MDBA dimethylamine salt= 50.0% by weight) and an aqueous Herbiace solution (an effective content of a bialaphos=20% by weight) was diluted 300 times to obtain 3 kinds of agricultural chemical formulations per effective component.

For a hothouse test, a fertilized soil sampled from a paddy field, a river sand and a commercial cultivated soil were mixed at 7:2:1 (weight ratio), and the mixed soil was then put in pots having an inner diameter of 12 cm. The seeds of crabgrass were planted in the pots, and they were allowed to germinate. In order to heighten the uniformity of the crabgrass among the pots, the pots in which the crabgrass abnormally grew were disposed of. The pots in which the crabgrass grew to a height of about 18 cm were used for the test. An agricultural chemical formulation was sprayed at a ratio of 10 liters per are by the use of a spray gun (Iwata Tosouki Kogyo Co., Ltd., RG type) so as to apply uniformly all over the crabgrass, and a herbicidal effect was evaluated.

A weight of the portion of the crabgrass on the ground was weighed on the tenth day from the spray treatment, and the evaluation of the herbicidal effect was shown by a herbicidal percent on the basic of a weight of the portion of the crabgrass on the ground which was not treated (refer to the following formula). The herbicidal percents of the respective agricultural chemical formulations are shown in Table 3.

Herbicidal percent =

$$\frac{\text{the weight of the portion of the crabgrass on the ground which was not treated } (g) - \text{the weight of the portion of the crabgrass on the ground which was treated } (g)}{\text{the weight of the portion of the crabgrass on the ground which was not treated } (g)} \times 100 \, (\%)$$

TABLE 3

| Effective component No. | Herbicidal percent(%) | | |
|---|---|---|---|
| | Banvel D solution | an aqueous Herbiace solution | a round-up solution |
| Product of the present invention | | | |
| 1 | 85.6 | 84.4 | 89.9 |
| 2 | 88.3 | 86.9 | 94.5 |
| 3 | 96.5 | 88.9 | 82.1 |
| 4 | 85.0 | 83.2 | 90.6 |
| 5 | 83.5 | 89.4 | 96.6 |
| 6 | 86.4 | 85.6 | 91.1 |
| 7 | 87.9 | 84.6 | 93.2 |
| 8 | 88.6 | 85.5 | 94.6 |
| 9 | 85.4 | 89.7 | 98.6 |
| 10 | 84.6 | 90.1 | 95.0 |
| 11 | 91.0 | 84.9 | 94.9 |
| 12 | 93.2 | 87.9 | 93.2 |
| 13 | 89.9 | 88.6 | 96.6 |
| 14 | 81.5 | 85.0 | 95.5 |
| 15 | 94.3 | 86.5 | 94.7 |
| 16 | 84.3 | 84.6 | 96.9 |
| 17 | 87.6 | 81.2 | 91.1 |
| 18 | 82.1 | 87.6 | 95.6 |
| 19 | 89.6 | 88.8 | 97.6 |
| 20 | 91.2 | 85.6 | 93.2 |
| Comparative product | | | |
| 21 | 78.8 | 70.2 | 78.9 |
| 22 | 71.9 | 68.9 | 77.7 |
| No addition | 56.1 | 66.6 | 71.2 |

Example 2

Kanzawa mite female imagos were inoculated onto a leaf disc of bush bean repeatedly three times every 30 imagos per section, and they were grown at 25° C. for 24 hours. Afterward, the whole leaf disc was immersed in a test solution for 5 seconds and then taken out of the test solution, and it was then allowed to stand at 25° C. for 48 hours. Observation was then carried out, and an acaricidal percent was obtained on the basis of a section in which any treatment was not done (refer to the following formula). As acaricides, there were used 2000 times diluted solutions of Nissorum hydrate (an effective content of hexythiazox=10% by weight), Osadan hydrate 25 (an effective content of fenbutatin oxide=25% by weight), and as an effect enhancer for an agricultural chemical, the same agent as in Example 1 was used. Regulation was performed so that a concentration of the effective component of the effect enhancer for the agricultural chemical might be 0.1% by weight. In addition, with regard to a case where any effect enhancer for the agricultural chemical was not used, a similar procedure was conducted. The acaricidal percent was obtained in accordance with the following formula. The results are shown in Table 4.

Acardial percent =

$$\frac{\text{the number of the alive acarids in the untreated section} - \text{the number of the alive acarids in the treated section}}{\text{the number of the alive acarids in the untreated section}} \times 100 \, (\%)$$

TABLE 4

| Effective component No. | Acaricidal percent (%) | |
|---|---|---|
| | Nissorum hydrate | Osadan hydrate |
| Product of the present invention | | |
| 1 | 78.9 | 91.1 |
| 2 | 83.3 | 93.3 |
| 3 | 86.7 | 90.0 |
| 4 | 84.4 | 93.3 |
| 5 | 86.7 | 95.6 |
| 6 | 82.2 | 88.9 |
| 7 | 85.6 | 92.2 |
| 8 | 87.8 | 83.3 |
| 9 | 84.4 | 94.4 |
| 10 | 86.7 | 91.1 |
| 11 | 87.8 | 90.0 |
| 12 | 88.9 | 92.2 |
| 13 | 91.1 | 85.6 |
| 14 | 90.0 | 84.4 |
| 15 | 93.3 | 83.3 |
| 16 | 83.3 | 91.1 |
| 17 | 87.8 | 92.2 |
| 18 | 92.2 | 96.7 |
| 19 | 86.7 | 95.6 |
| 20 | 92.2 | 93.3 |
| Comparative product | | |
| 21 | 61.1 | 66.7 |
| 22 | 58.9 | 60.0 |
| No addition | 54.4 | 58.9 |

Example 3

The whole leaf disc of bush bean was immersed in a test solution for 5 seconds, and it was then taken out of the test solution. After the leaf disc was air-dried, 10 three-year grubs of a previously grown larvae were put on the leaf disc, and they were grown at 25° C. for 10 days. The number of deaths of the larvae was counted with the naked eye to Judge the effect of the insecticide. Incidentally, the test was carried out repeatedly three times, and an insecticidal percent was obtained in the same manner as in the case of the acaricidal percent. As the insecticide, there were used 2000 times diluted solutions of a commercially available Dimili hydrate (an effective content of diflubenzuron=23.5% by weight), an Applaud hydrate (an effective content of buprofezin=25% by weight), and as an effect enhancer for an agricultural chemical, the same agent as in Example 1 was used. Prior to the use, the effect enhancer was regulated so that its concentration in a diluted solution might be 0.1% by weight. The results are shown in Table 5.

TABLE 5

| Effective component No. | Insecticidal percent (%) | |
|---|---|---|
| | Dimili hydrate | Applaud hydrate |
| Product of the present invention | | |
| 1 | 83.3 | 96.7 |
| 2 | 86.7 | 96.7 |
| 3 | 93.3 | 96.7 |
| 4 | 90.0 | 93.3 |
| 5 | 86.7 | 93.3 |
| 6 | 93.3 | 90.0 |
| 7 | 90.0 | 86.7 |
| 8 | 90.0 | 93.3 |
| 9 | 86.7 | 93.3 |
| 10 | 86.7 | 93.3 |
| 11 | 93.3 | 86.7 |
| 12 | 90.0 | 93.3 |
| 13 | 86.7 | 83.3 |
| 14 | 83.3 | 83.3 |
| 15 | 86.7 | 83.3 |
| 16 | 90.0 | 90.0 |
| 17 | 86.7 | 93.3 |
| 18 | 80.0 | 96.7 |
| 19 | 90.0 | 96.7 |
| 20 | 93.3 | 96.7 |
| Comparative product | | |
| 21 | 66.7 | 66.7 |
| 22 | 60.0 | 60.0 |
| No addition | 56.7 | 56.7 |

Example 4

A spore suspension ($10^7$ spores/ml) of cucumber grey Botrytis cinerea which were bactericide-resistant bacteria was sprayed onto cucumber juvenile seedling (3 main leaves were being developed) every 10 ml of the spore suspension per pot, and it was then allowed to stand at 25° C. and a relative humidity of 90% for one day.

Afterward, a Benlate hydrate (an effective content of benomyl=50% by weight) which was a commercially available bactericide was diluted to 2000 times with a 2500 times diluted solution of an effect enhancer for an agricultural chemical used in Example 1, and it was sprayed every 5 ml per pot. Afterward, it was allowed to stand at 25° C. and a relative humidity of 85%, and the number of lesions was counted and a prevention value to an untreated section was obtained by the following formula. The results are shown in Table 6.

$$\text{prevention value} = \left(1 - \frac{\text{lesion No. of the crabgrass on the ground which was treated}}{\text{lesion No. of the crabgrass on the ground which was not treated}}\right) \times 100$$

TABLE 6

| Effective component No. | Prevention value Benlate hydrate |
|---|---|
| Product of the present invention | |
| 1 | 75 |
| 2 | 85 |
| 3 | 80 |
| 4 | 75 |
| 5 | 88 |
| 6 | 80 |
| 7 | 77 |
| 8 | 84 |
| 9 | 78 |
| 10 | 81 |
| 11 | 82 |
| 12 | 86 |
| 13 | 81 |
| 14 | 88 |
| 15 | 79 |
| 16 | 81 |
| 17 | 83 |
| 18 | 85 |
| 19 | 90 |
| 20 | 92 |
| Comparative product | |
| 21 | 75 |
| 22 | 77 |
| No addition | 60 |

Examples 1 to 4 show a case where the effect of the effect enhancer for the agricultural chemical regarding the present invention is compared with a case (a comparative product) where a usual nonionic surfactant is used as an effect enhancer for an agricultural chemical. As is apparent from Tables 1 to 5, the effect enhancer for the agricultural chemical regarding the present invention noticeably exerts the effect, and so it is at a practical level, but in the comparative product, a slight effect increase of the agricultural chemical is observed, not being at the practical level. Therefore, it can be understood that the effect enhancer for the agricultural chemical regarding the present invention can specially improve the effect of the agricultural chemical as compared with an usual nonionic surfactant.

Example 5

Table 7 shows a prescription example where a product of the present invention is used as emulsifiers•dispersants for agriculture. In addition, Table 8 shows examples where emulsions are prepared by the use of these emulsifiers•dispersants, and the results of the emulsifying•dispersing properties in these cases. Incidentally, in Table 8, test procedures of the self emulsifying properties and the emulsifying•dispersing properties are as follows.

Self Emulsifying Properties

Two or three drops of an agricultural chemical formulation were added to a hard water, and the dispersion state of the agricultural chemical formulation was then observed by the naked eye and an evaluation was made on the basis of the following standards. In this case, as the hard water, Germany hard water (containing a Ca ion and a Mg ion) was used. One degree of Germany hardness means that 10 g of CaO is dissolved in 1 m³ of water, and Mg is converted into CaO in a ratio of 1.4 MgO=1 CaO.

A: The agricultural chemical formulation slowly dropped, while it was emulsified and diffused.

B: The agricultural chemical formulation was emulsified, but it straightly dropped.

C: Oil drop.

Emulsifying•Dispersing Properties

After the test of the self emulsifying properties, the agricultural chemical formulation was diluted 1000 times by weight with the same hard water as the aforementioned, followed by stirring by a glass rod. Afterward, the agricultural chemical formulation was observed by the naked eye, and then evaluated on the basis of the following standards.

A: An emulsifying state which emits a bluish white fluorescent light.

B: A white emulsifying state.

C: Oil state.

TABLE 7

|  | Emulsion prescription Product -1 of the present invention | Emulsion prescription Comparative compound -1 of the present invention | Emulsion prescription prescription Product -2 of the present invention | Emulsion prescription Comparative compound -2 of the present invention |
|---|---|---|---|---|
| Calcium alkylbenzenesulfonate | 30.0 | 30.0 | 26.3 | 26.3 |
| Calcium petroleum sulfonate |  |  |  |  |
| POE(18) styrenated phenol ether | 32.0 | 32.0 |  |  |
| POE(15) tribenzyl phenol ether |  |  | 40.3 | 40.3 |
| POE(30) tribenzyl phenol ether |  |  | 7.2 | 7.2 |
| Sorbitan trioleate |  |  |  |  |
| ② compound |  |  | 10.5 |  |
| ③ compound | 20.0 |  |  |  |
| Comparative product [POE(11) nonyl phenyl ether] |  | 12.0 |  | 10.5 |
| Comparative product [POE(18) nonyl phenyl ether] |  | 8.0 |  |  |
| Xylene | 18.0 | 18.0 | 15.7 | 15.7 |

TABLE 8

|  |  | Sumithion | | Malathon | |
|---|---|---|---|---|---|
|  |  | Emulsion prescription Product-1 of the present invention | Emulsion prescription Comparative compound-1 of the present invention | Emulsion prescription Product-2 of the present invention | Emulsion prescription Comparative compound-2 of the present invention |
| A technical grade of active ingredient for an agricultural chemical | | 50.0 | 50.0 | 50.0 | 50.0 |
| Emulsifier | | 10.0 | 10.0 | 10.0 | 10.0 |
| Xylene | | 40.0 | 40.0 | 40.0 | 40.0 |
| Self emulsifying properties | 10 German hard water | A | B | B | B |
| | 19 German hard water | A | B | B | B |
| Emulsifying dispersing properties | 10 German hard water | A | A | A | A |
| | 19 German hard water | A | A | A | A |

What is claimed is:

1. A composition comprising, a compound represented by formula (I):

$$R-O[(EO)_x(PO)_y](EO)_z-H \qquad (I)$$

wherein EO is an oxyethylene group; PO is an oxypropylene group; R is a, straight-chain or branched alkyl group or alkenyl group having 6 to 30 carbon atoms; x is a value of 1 to 30 on the average; y is a value of 1 to 30 on the average; z is a value of 1 to 30 on the average; and the copolymer $-[(EO)_x(PO)_y]-$ may be a random copolymer or a block copolymer; and a technical grade of an active ingredient or an active compound for an agricultural chemical.

2. The composition according to claim 4, further comprising a surfactant other than the compound represented by formula II).

3. The composition according to claim 4, further comprising a chelating agent.

4. The composition according to claim 1, wherein the weight ratio of the compound represented by formula (I) to technical grade of active ingredient or active compound for an agricultural chemical is 0.03 to 50.

5. The composition according to claim 1, wherein the weight ratio of the compound represented by formula (I) to technical grade of active ingredient or active compound for an agricultural chemical is 0.04 to 20.

6. The composition according to claim 1, wherein the weight ratio of the compound represented by formula (I) to technical grade of active ingredient or active compound for an agricultural chemical is 0.1 to 10.

7. A method of preparing the compound represented by formula (I) in claim 4, the compound represent by formula (I) is obtained by first adding ethylene oxide and propylene oxide to an alcohol having the formula R—OH to obtain R—O[(EO)$_x$(PO)$_y$]—H and then adding ethylene oxide thereto.

8. A method of preparing the compound represented by formula (I) in claim 4, the compound represented by formula (I) is obtained by first adding ethylene oxide to an alcohol having the formula R—OH to obtain R—O—(EO)$_x$—H, then adding propylene oxide to obtain R—O[(EO)$_x$(PO)$_y$]—H and finally, adding ethylene oxide thereto.

9. A method for enhancing the effect of an agricultural chemical which comprises the step of feeding a compound represented by the general formula (I) together with the agricultural chemical to a site where the effect of the agricultural chemical is required:

$$R\text{—}O[(EO)_x(PO)_y](EO)_z\text{—}H \qquad (I)$$

wherein EO is an oxyethylene group; PO is an oxypropylene group; R is a straight-chain or branched alkyl group or alkenyl group having 6 to 30 carbon atoms; x is a value of 1 to 30 on the average; y is a value of 1 to 30 on the average; and z is a value of 1 to 30 on the average.

10. The method according to claim 1 wherein a surfactant other than the compound represented by the formula (I) is also further fed.

11. The method according to claim 1 wherein one or more of the compounds described in claim 1 and 0.01 to 30 mols of a chelating agent per mol of the compound are also fed.

12. The method according to claim 1, wherein the copolymer —[(EO)$_x$(PO)$_y$]— of the compound represented by formula (I) is a block copolymer.

* * * * *